(12) United States Patent
Lundberg et al.

(10) Patent No.: US 6,284,271 B1
(45) Date of Patent: Sep. 4, 2001

(54) MULTIPLE UNIT EFFERVESCENT DOSAGE FORM

(75) Inventors: Per Johan Lundberg; Mikael Thune, both of Mölndal (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/125,933

(22) PCT Filed: Jun. 22, 1998

(86) PCT No.: PCT/SE98/01209

§ 371 Date: Aug. 28, 1998

§ 102(e) Date: Aug. 28, 1998

(87) PCT Pub. No.: WO99/01112

PCT Pub. Date: Jan. 14, 1999

(30) Foreign Application Priority Data

Jul. 1, 1997 (SE) .................................... 9702533

(51) Int. Cl.[7] ................ A61K 9/46; A61K 9/48; A61K 9/16
(52) U.S. Cl. ................ 424/466; 424/452; 424/494; 424/497
(58) Field of Search ................ 424/451, 466, 424/452, 494, 497

(56) References Cited

U.S. PATENT DOCUMENTS

| | | |
|---|---|---|
| 4,786,505 | 11/1988 | Lovgren et al. . |
| 4,814,178 | 3/1989 | Bolton et al. . |
| 4,844,905 | * 7/1989 | Ichikawa et al. . |
| 4,927,640 | 5/1990 | Dahlinder et al. . |
| 5,445,826 | 8/1995 | Kuhrts . |

FOREIGN PATENT DOCUMENTS

| | | |
|---|---|---|
| 0257310 | 3/1988 | (EP) . |
| 0297978 | 1/1989 | (EP) . |
| 0667149 | 8/1995 | (EP) . |
| 0669129 | 8/1995 | (EP) . |
| 0670160 | 9/1995 | (EP) . |
| 1507521 | 4/1978 | (GB) . |
| 9410994 | 5/1994 | (WO) . |
| 9421239 | 9/1994 | (WO) . |
| 9527482 | 10/1995 | (WO) . |
| 9601621 | 1/1996 | (WO) . |
| 9601623 | 1/1996 | (WO) . |
| 9725030 | 7/1997 | (WO) . |

OTHER PUBLICATIONS

Stevens, et al., Chem. Abstracts Selects 123: p. 30, Abstract No. 179493w (1995).
Kanbe, et al., Chem. Abstracts Selects Plus 124: p. 45, Abstract No. 97775w (1996).
Machoczek, Chem. Abstracts Selects Plus 124: p. 45, Abstract No. 97777y (1996).
Yuasa, et al., Chem. Pharm. Bull. 44 (7), pp. 1361–1366 (1996).
Atyabi, et al., Journal of Controlled Release 42, pp. 25–28 (1996).
Atyabi, et al., Journal of Controlled Release 42, pp. 105–113 (1996).
Simoni, et al., Pharmacological Research 31, No. 2, pp. 115–119 (1995).

* cited by examiner

Primary Examiner—Thurman K. Page
Assistant Examiner—Blessing Fubara
(74) Attorney, Agent, or Firm—White & Case LLP

(57) ABSTRACT

The present invention is related to an effervescent pharmaceutical preparation comprising effervescent excipients and a plurality of individual units comprising a pharmaceutically active compound and optional excipients wherein the units (1) are provided with a floating generating system. The floating generating systems comprises at least two coating layers, one of which is a gas generating layer (2) and the other layer is a barrier layer (3) enclosing the generated gas. Furthermore the invention is related to a process for the manufacture of the dosage forms, and their use in medicine.

10 Claims, 2 Drawing Sheets

MULTIPLE UNIT EFFERVESCENT DOSAGE FORM

FIELD OF THE INVENTION.

The present invention relates to a novel pharmaceutical preparation in the form of a multiple unit effervescent dosage form comprising at least one pharmaceutically active substance, i.e. the drug(s). The effervescent dosage form comprises a drug and optionally pharmaceutically acceptable excipients in the form of individual units which units are layered with at least two coating layers providing a floating generating system. A plurality of these units with the floating generating system are mixed together with effervescent excipients and filled into a sachet or, preferably compressed into a multiple unit tableted dosage form.

More specifically, the invention relates to a new effervescent dosage forms comprising individual units, which units are coated with at least two coating layers and which layers make the individually coated units to float when they are liberated in an aqueous effervescent solution. These new effervescent dosage forms comprise for instance units of an acid susceptible substance, such as a proton pump inhibitor protected by an enteric coating layer, or comprise units of a substance which may cause irritation of the mucosal area, or comprise units of a substance covered by a film coating resulting in a controlled release profile, such as an extended release profile. Furthermore, the present invention refers to a method for the manufacture of such dosage forms and, to the use of such dosage forms in medicine.

BACKGROUND OF THE INVENTION AND PRIOR ART

Effervescent dosage forms are one possible vehicle for the administration of drugs. Effervescence may be used to provide some degree of taste-masking. Prior to administration to a patient, an effervescent composition is dissolved and/or dispersed in e.g. an aqueous medium, such as drinking water. Dissolution and/or dispersion takes place directly or rapidly, with effervescence to give an agreeable presentation of the drug in the form of a solution which is suitable to drink. Effervescent dosage forms are particularly suitable for patients finding difficulty in swallowing tablets or disliking tablets.

The dissolution upon effervescence of a multiple unit tablet that gives a dispersion of drug particles, or of individual units comprising the drug may cause problem due to the density of the units and/or the density of coating layers surrounding the units. One problem might be that a majority of the individual units are sinking to the bottom of the drinking glass during or/and after effervescence, but prior to administration. These sinking units make it difficult for the patient to drink the dispersion and to receive the complete dose because a great number of the drug containing units will remain in the glass.

A further problem with effervescent tablets is the composition of effervescent tablet excipients which might cause problem to the incorporated drug. For instance, the use of an acidic substance in the effervescent composition presents a problem, if the drug is an acid susceptible compound, such as a proton pump inhibitor. The prior art has already taught that such an acid susceptible drug is best protected by an enteric coating layer. There are different enteric coating layered preparations of for instance omeprazole as well as of other proton pump inhibitors described in the prior art, e.g. U.S. Pat. No. 4,786,505 (AB Hässle). A tableted multiple unit dosage form must also fulfill standard requirement on enteric coated articles. A suitable tableted multiple unit dosage form comprising omeprazole is described in EP 95926054.8 (Astra AB). Incorporation of such enteric coated pellets in an effervescent tablet are described in the International patent application WO97/25030 filed on Dec. 20, 1996 (Astra AB).

Other groups of drugs prepared in dosage forms with coating layer(s) are for instance substances irritating the mucosal area, e.g. NSAIDs (Non Steroidal Anti-inflammatory Drugs), and drugs formulated into controlled release dosage forms, e.g. extended release formulations.

Some examples of different effervescent tablets and systems described in the prior art are discussed below.

Effervescent tablets containing acid-sensitive agents have previously been made by coating the acid particles in the acid-base couple with the base to separate the acid-sensitive agent from the acid, see WO 94/21239 (Wehling et al.) Effervescent tablets containing the active substance without any coating layer have also been suggested by Wehling et al.

Another construction principle has been presented, wherein extended release microcapsules are incorporated in an effervescent tablet, see WO 95/27482 (Elan corp.) A further example is the above mentioned WO097/25030.

Stomach-floating hard-gelatine capsules have been described by Simone et al in Pharmacol. Res. 1995, 31(2), 115–19. However, this capsule preparation is not an effervescent dosage form, i.e. the preparation does not comprise any effervescent components.

The expandable controlled release dosage form described in EP 669 129 is using gas development in a dosage form. The tablet swells to such a size that it stays for a prolonged time in the stomach by utilising the gas generated after ingestion of the tablet.

None of the above discussed prior art document describes or discuss problems involved with dense units in an effervescent dosage form, such as an effervescent tablet comprising a plurality of individual units.

SUMMARY OF THE INVENTION

The present invention provides individually floating units comprising a pharmaceutically active substance by applying at least two coating layers, named as a floating generating system. These floating units are intended for an effervescent dosage form, and avoid the problems with units sinking during and after effervescence. The first layer of the floating generating system comprises a gas source, which reacts with an acidic aqueous solution to generate gas. The acidic aqueous solution originating from the surrounding effervescent solution penetrates through the second (outer) layer of the floating generating system. The second layer also provides a barrier to enclose the generated gas. The enclosed gas causes the density of the units to decrease, and the units will float in the effervescent solution.

More specifically, the present invention provides a multiple unit effervescent dosage form comprising individually coated units comprising a drug, and effervescent excipients. The multiple unit dosage form can be in the form of a sachet comprising the units coated according to the present invention, and the effervescent excipients, or in the form of a tableted dosage form, wherein the same coated units together with effervescent tablet excipients are compressed into a tablet.

The individually coated units containing the drug will float for a time longer than the time needed for the effervescence and liberation of the units. Thereby, the invention avoids the problem with dense units sinking to the bottom of a drinking glass during administration of the dosage form.

Further, the present invention provides a new floating generating system for effervescent dosage forms comprising a gas generating coating layer composition, and a barrier layer to enclose generated gas.

The floating effect is provided for a time long enough for the patient to complete the administration i.e. the reaction of the effervescent components with the drinking water, and to ingest the dispersion without a hurry. More specifically the floating effect is provided during approximately 5 minutes.

DETAILED DESCRIPTION OF THE DRAWINGS

FIG. 1 shows a cross-view of a three-layered unit according to the invention. The enteric coated unit 1 is coated with a floating generating system comprising a gas generating layer 2, and a gas barrier layer 3.

FIG. 2 shows a cross-view of a four-layered unit according to the invention. The enteric coated unit 1 is coated with a separating layer 4, and a floating generating system comprising a gas generating layer 2, and a gas barrier layer 3.

DETAILED DESCRIPTION OF THE INVENTION

Figure 1:
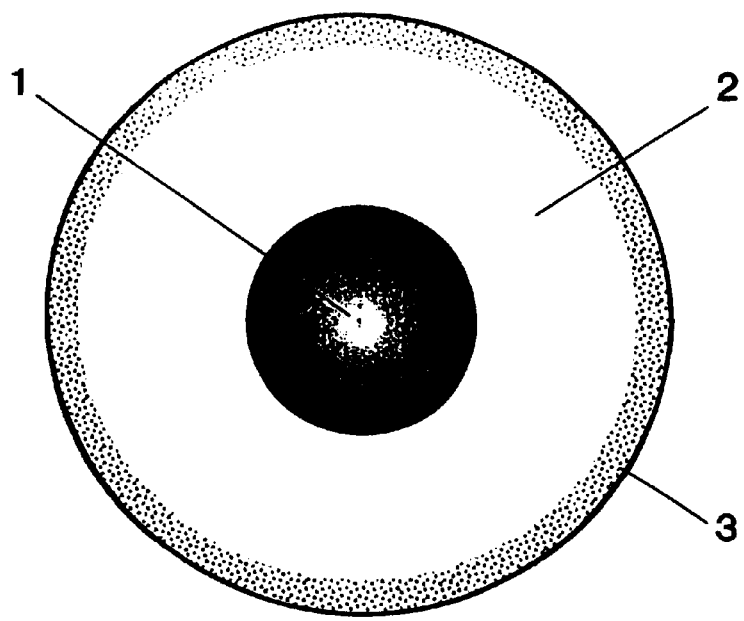
Figure 2:
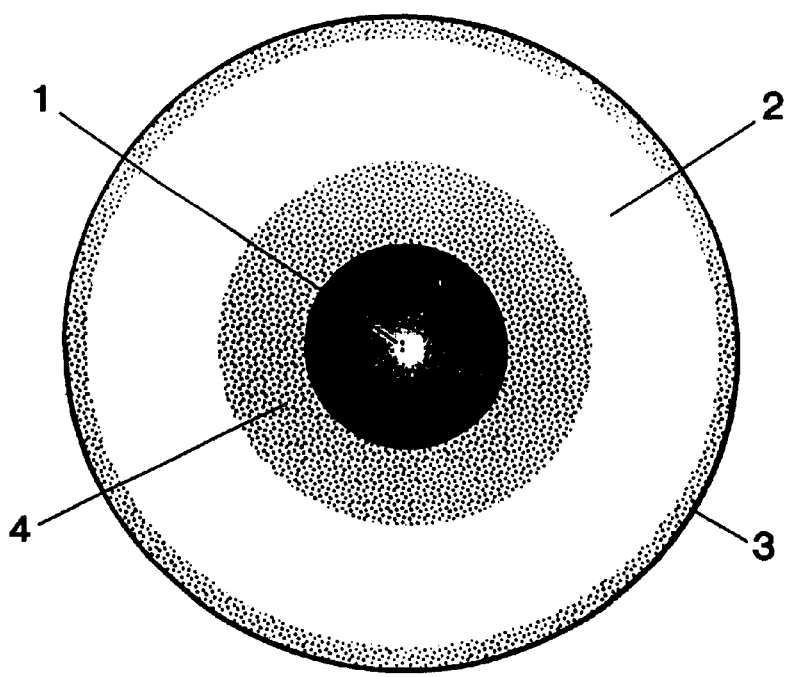

The units with a floating generating system according to the present invention are to be mixed with effervescent excipients into a multiple unit effervescent dosage form. The drug containing units are coated with at least two coating layers providing the floating generating system. The first layer, i.e. the inner layer of the floating generating system comprises a gas generating component, i.e. a gas source, which component generates gas bubbles by a reaction between the gas generating component and the acidic aqueous solution penetrating into that layer. The acidic aqueous solution originates from the surrounding effervescent solution. The second layer, i.e. the outer coating layer of the floating generating system permits the permeation of aqueous solution, but restricts the out passage of the generated gas bubbles through the layer.

The coated units are mixed with effervescent excipients, in the form of a powder mix or granulate. These effervescent excipients, i.e. effervescent granulate/mix, must not upon dissolution in water, result in a solution with a pH value dissolving or destroying any protecting coating layer, such as for instance an enteric coating, applied onto the drug units. Preferably, the effervescent solution will receive a pH value of less than 5 upon effervescence in an aqueous solution, such as drinking water.

The dosage forms according to the invention are characterised by rapidly dissolving in an aqueous solution liberating a plurality of individually floating units. Furthermore, they may contain taste improving agents, colorants, pharmaceutically acceptable additives such as lubricating agents, disintegrants and wetting agents.

The coating layer system achieving a floating generating system is especially suitable for effervescent dosage forms comprising units/pellets which will sink during and/or after effervescence due to their density. The units/pellets may be of the following types: extended release pellets, enteric coated pellets, taste masked pellets or any combination thereof.

Optionally, a separating layer is applied onto the individual units before the floating generating system is applied. Thus, if the outer surface of the drug containing unit is incompatible with any component used in the gas generating layer, there might be a need to apply a separating layer prior to the application of the two layers of the floating generating system.

The need of a separating layer can be exemplified with pellets having an enteric coating polymer applied as the outer layer of the drug containing units, which enteric coating may be negatively affected by a direct contact with an alkaline inner layer of the floating generating system, e.g. a layer containing sodium bicarbonate.

Drugs suitable for the dosage form according to the present invention are such drugs, which will be absorbed from the gastrointestinal channel or will act locally therein. Such suitable drugs can be selected from the following groups.

Antiulcer drugs such as proton pump inhibitors, $H_2$-antagonists or prostaglandins, e.g. drugs known by the generic names omeprazole, lansoprazole, pantoprazole, rabeprazole, cimetidine, ranitidine, famotidine and misoprostol etc. Spasmolytic drugs e.g. papaverin. Motility stimulating drugs e.g. cisapride, mosapride and metoclopramide. Antiemetic drugs e.g. granisertron and ondansertron. Bile acids or bile salts e.g. cholic acid. Laxative drugs e.g. bisakodyl. Antidiarrheal drugs e.g. loperamide. Drugs for intestinal inflammations e.g. mesalazine, olsalazine and sulfasalazine. Hyper- and hypoglycemic agents e.g. metformine, chlorpropamide, glibenklamide, glipizide and tolazamide. Nutritional additives such as vitamins and minerals, e.g. phytomenadion, thiamine, and pyridoxine. Anticoagulant drugs e.g. dicumarol, warfarine, dipyramidole and ticlopidine. Antianemetic drugs e.g. cyanocobolamine and folic acid. Lipid lowering drugs such as ninotinic acid, gemfibrozil, niceritrole, pravastastine, simvastatine and fluvastatine. Cardiac glycosides e.g. digitoxin, digoxin and proscillaridine. Cardiac stimulating agents other than glycosides e.g. etilefrine and amrinone. Antiarrhythmic drugs e.g. quinidine, disopyramide, procaineamide, mexiletin, tocainide, flecainide, propafenone and amiodarone. Coronary vasodilators such as nitrates, e.g. isosorbide mononitrate and glyceryl nitrate. Antihypertensive agents such as cerebral vasodilators and peripheral vasodilators e.g. clonidine, prazosine, hydralazine; such as ACE-inhibitors e.g. ramiprile, enalaprile and lisinoprile; such as renin-inhibitors e.g. losartane and candesartane. Diuretics e.g. bumetanide, furosemid, spironolactone, amilorid and chlorothalidone. β-blocking agents e.g. alprenolol, pindolol, propranolol, sotalol, timolol, atenolol, metoprolol and labetalol. Ca-channel blocking agents e.g. amlodipine, felodipine, nicardipine, nifedipine, verapamil and diltiazem. Antibiotics such as amoxicillin, bacampicillin, dicloxacillin, chlarithromycine, doxycycline, cefuroxim, erythromycine, norfloxacine and ofloxacine. Other antibacterial and antimycotical drugs e.g. metronidazole, fusidinic acid, nitrofurantoin, trimetoprime, and sulphonamides e.g. sulfadiazine sulfamethoxazole or ketoconazole. Corticosteroids e.g. deflazacort, cortisone, prednisolon, prednison and budesonide. Thyroid and anti-thyroid preparations such as levothyroxine, liothyronine, propylthiouracil and thiamazole. Antiviral agents e.g. aciclovir. Anti-inflammatory substances such as non-steroidal anti-inflammatory substances e.g. diclofenac, ibuprofen and piroxicam. Muscle relaxant drugs e.g. chlorzoxazone. Analgesics such as dextropropoxiphene, acetylsalicylic acid, acetaminophen and paracetamol. Antimigraine drugs e.g. ergot alkaloids. Anticonvulsants e.g. phenytoin and carbamazepine. Anti-Parkinson drugs e.g. metixene. Neuroleptic drugs e.g. chlorpromazine and dixyrazine. Sedatives and tranquilizers such as diazepam, oxazepam and flunitrazepam. Stimulants e.g. caffeine. Smoke-cessation helping agents e.g. nicotine. Anthelmintics e.g. mebendazole. Decongestants e.g. phenylpropanoleamine and pseudoephedrine. Anti-asthmatics such as terbutaline, bambuterole and theophylline. Antihistamines e.g. brompheniramine and terfenadine.

The above listed pharmaceutically active compounds may be used in a non-salt form, or in the form of a pharmaceutically acceptable salt thereof. If the compound exists as optically antipodes, i.e. in an optically pure form, they can be used in the form of a racemic mixture or in the form of one of the single enantiomers thereof, either in a salt form or in a non-salt form.

The above discussed substances may be in the form of granules, or in the form of units with a modified release profile, such as enteric coated units, units having a diffusion controlling membrane or erosion controlled units. The drug containing units intended to be covered by the floating generating system, have a suitable size in the range of 0.1 to 2 mm in diameter.

The two layers forming the floating generating system are applied onto the units containing the drug. The inner layer of the system is a gas generating layer comprising a gas generating source and a binding agent.

As gas generating sources the following components may be used according to the present invention: a carbon dioxide or oxygen generating source. A carbonate or a bicarbonate reacting with the acidic solution penetrating from the effervescent solution surrounding the liberated units is preferred as the carbon dioxide generating source. Such suitable carbon dioxide generating sources are for instance sodium bicarbonate and sodium carbonate. For instance sodium percarbonate and copper sulphate anhydrous are preferred as the oxygen generating source. The oxygen generating reaction starts when aqueous solution from the surrounding effervescent solution penetrates through the barrier layer.

The following water soluble binders are suitable in the gas generating layer, a polymeric compound such as for instance hydroxypropyl methylcellulose (HPMC), hydroxypropylcellulose LF, solid polyoxyethylenglycols, such as PEG 6000 or PEG 20M, or polyvinyl pyrrolidone, or other pharmaceutically acceptable water soluble binders, such as for instance sugars.

The gas generating layer has to be covered by a layer being the outer layer of the floating generating system, and functioning as a barrier for the generated gas. Materials suitable for this outer, barrier layer are non-water soluble polymeric compounds like enteric coating polymers, such as for instance metacrylic esters co-polymers, hydroxypropyl metylcellulose acetate succinate (HPMCAS), and other non-water soluble polymers with incorporation of water soluble pore forming substances. Such pore forming substances are for instance sugars such as sucrose, or any of the water soluble polymers listed above. The expression water soluble refers to the definition of soluble including up to very soluble in the US Pharmacopoeia USP XXII (1990).

Suitable material for the separating layer optionally applied and acting as a buffer layer between the units and the inner layer of the floating generating system, are water soluble polymers, hydroxypropyl metylcellulose, or solid polyethylenglycols. The polymers are optionally in admixture with a suitable pH-buffering substance e.g. succinic acid or tartaric acid.

The two layers of the floating generating system according to the present invention can be applied by coating or layering procedures in a suitable equipment, such as in a fluidized bed, a coating granulator or in a coating pan. The amount of applied layers will depend on the product to be manufactured and the process conditions for the polymeric material used. The units containing the pharmaceutically active compound can be manufactured according to different principles, such as described in for instance U.S. Pat. No. 4,927,640 or WO96/01623 which documents hereby are incorporated by references.

The effervescent dosage forms contain, in addition to the units covered with the floating generating system, effervescent excipients, such as a source of carbon dioxide in combination with an acid, or other effervescent system known by a person skilled in the art. The effervescent excipients used in the dosage form according to the present invention must not interfere in a disadvantagely manner with the coated units in the prepared dosage form. The buffering components of the effervescent excipients can generally be divided into two categories; a carbon dioxide source and an acidic component. The latter reacts in presence of water with the carbon dioxide source resulting in the development of carbon dioxide gas. The effervescent excipients may also include other excipients such as for instance binding agents, diluents, lubricants, disintegrating agents, surfactants, taste improving agents, colorants or the like.

As carbon dioxide source can be used for instance alkali metal carbonates or bicarbonates, alkaline earth metal carbonates or bicarbonates, or other inorganic salts containing carbonate or bicarbonate ions. As acidic components suitable to incorporate in the dosage form is effervescent excipients are preferably solid acidic compounds, such as for instance monosodium dihydrogen phosphate, or tartaric acid, citric acid and other weak organic acids.

The manufacture of the multiple unit effervescent dosage form according to the present invention can be done in the following manner by a process comprising the following steps:

a) forming a unit comprising a pharmaceutically active compound, b) optionally covering the unit of step a) with a buffering and separating layer, c) covering the unit of step a) or step b) with a gas generating layer, d) covering the coated unit of step c) with a barrier layer, e) mixing a plurality of the units prepared in step d) with effervescent excipient, and f) either filling the mixture into a sachet or compressing the mixture into a tablet form.

The effervescent dosage forms according to the invention are suitable for oral administration. The dose, and dose frequency, will depend on the nature and severity of the disease to be treated. The dose may also vary according to the age, body weight, and response of the individual patient. Children and patients with liver diseases as well as patients under long term treatment will generally benefit from doses that are somewhat lower than the average.

The invention is described more in detail by the following non- limiting examples and the accompanying drawings.

EXAMPLE 1

Effervescent tablet comprising pellets of metoprolol succinate with extended release. Tablet strength 95 mg metoprolol succinate.

Principle.

Extended release metoprolol succinate (MSER) pellets were coated with two additional layers, i.e. the floating generating system, providing a floating effect to the pellets when exposed for an acidic solution. The first layer comprises sodium bicarbonate as a gas source, and the second layer is utilised as a barrier layer binding the generated carbon dioxide gas bubbles in the prepared pellets. These metoprolol succinate floating extended release (MSFER) pellets was compressed with an effervescent tablet excipient granulate into a tablet. When the tablet is dissolved in a glass of water, an effervescent solution is obtained. The resulting solution of the effervescent dispersion had a pH value of about 5.

Preparation of Metoprolol Succinate-ER (MSER) Pellets

A solution of metoprolol succinate (126 kg dissolved in 210 kg water) was spray-crystallised on $SiO_2$-cores (30 kg) in a fluidized bed. The obtained pellets had a metoprolol succinate content of approximate 800 mg/g.

These metoprolol succinate units/cores were coated with an extended release film coating solution in a fluidized bed as described below.

| Preparation of coated cores: | |
|---|---|
| metoprolol succinate cores | 10.0 kg |
| Composition of extended release solution: | |
| ethyl cellulose 10 cps | 4.2 kg |
| hydroxypropyl cellulose LF | 1.3 kg |
| ethanol 95% (w/v) | 26.8 kg |

The MSER pellets are prepared as described in U.S. Pat. No. 4,927,640 hereby incorporated in a whole by reference.

| Preparation of metoprolol succinate floating ER (MSEER) pellets | |
|---|---|
| MSER pellets prepared according to above | 200 g |
| Composition of bicarbonate solution for gas generating layer: | |
| hydroxypropyl methylcellulose 6 cps | 16 g |
| sodium bicarbonate | 64 g |
| water purified | 800 g |

The MSER pellets were coated with the bicarbonate solution in a Wurster equipped fluidized bed. The obtained product was then further coated in the same equipment with a second additional layer providing a barrier for the generated gas.

| MSER pellets layered with bicarbonate | 100 g |
|---|---|
| Composition of barrier layer: | |
| hydroxypropyl methylcellulose acetate succinate LF | 10.0 g |
| polyethylene glycol 400 | 2.0 g |
| methanol anhydrous | 210 g |

The content of metoprolol succinate in the obtained MSFER pellets was 366 mg/g pellets.

| Preparation of metoprolol succinate effervescent extended release tablets | |
|---|---|
| | mg/tablet |
| MSFER pellets prepared according to above | 260 |
| citric acid anhydrous | 519 |
| sodium bicarbonate | 382 |
| polyvinylpyrrolidone (= PVP) K-25 | 34 |
| sorbitol | 600 |
| sodium carbonate anhydrous | 30 |
| sodium laurylsulphate | 1.5 |
| sodium stearylfumarate | 14 |
| ethanol 99.5% | 516 |
| water | 58 |

The citric acid and sodium bicarbonate was granulated with a solution of the PVP dissolved in a mixture of the ethanol and the water.

The granules were dried at 55° C. over night on trays in a drying cabinet. The granules were milled with a conical sieve mill having 1.14 mm openings.

In a suitable mixer the sodium stearylfumarate, sodium laurylsulphate, sodium carbonate and the sorbitole was mixed to homogenity. Thereafter, the milled granules of citric acid and sodium bicarbonate were admixed and finally also the MSFER pellets.

Tablets with a weigh of 1840 mg and containing 95 mg of metoprolol succinate were compressed on a tableting machine equipped with 20 mm in diameter flat punches with bevelled edge.

Test of Tablets.

Dissolution rate of metoprolol succinate from the tablets was measured in 500 ml phosphate buffer pH 6.8, 37° C., using USP dissolution apparatus 2 (paddle), operated at 100 r.p.m.

Figure 3:
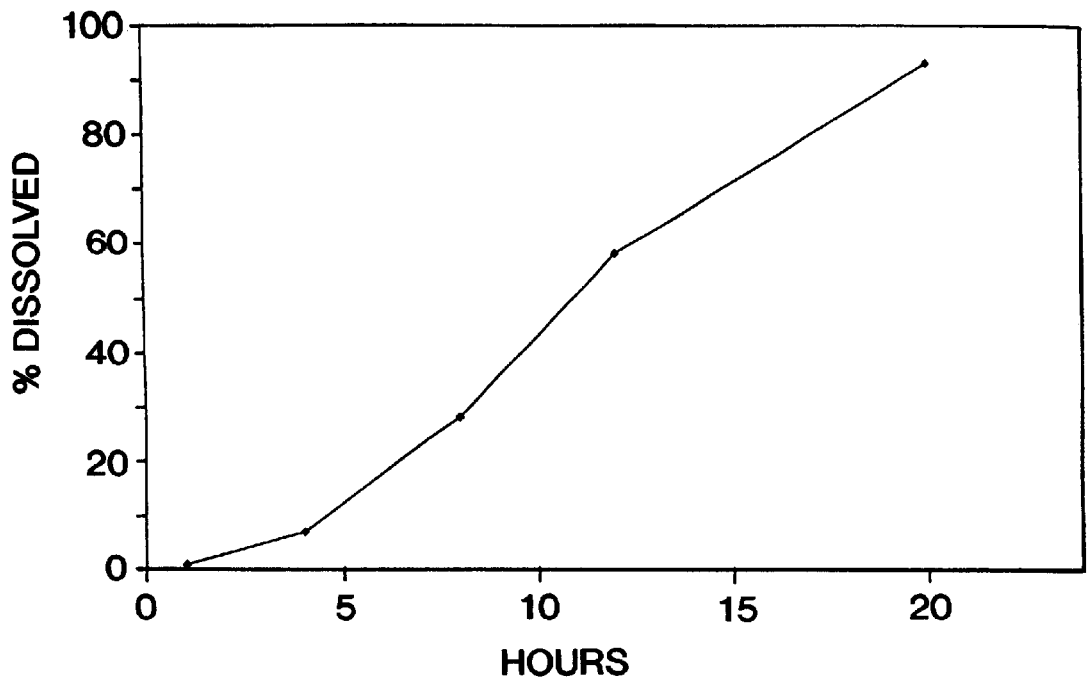
FIG. 3 shows the dissolution of metoprolol succinate from a tableted effervescent dosage form according to the present invention, as described in example 1 below.

The dissolution of metoprolol succinate from the effervescent tablet, average 4, is shown in FIG. 3.

Floating Behaviour

Comparison of pellets with and without a floating generating system.

| | MSER (from Ex. 1.) | MSFER (with) (from Ex. 1.) |
|---|---|---|
| Density* | 1.28 g/ml | 1.35 g/ml |
| Test in buffer pH 5 | all are sinking | after 15–20 sec. all are floating |

*Micromeritics multivolume pycnometer 1305 operated with helium. (Gasadsorption according to B.E.T.)

EXAMPLE 2

Effervescent tablet comprising enteric coated omeprazole pellets. Tablet strength 20 mg omeprazole.

Principle.

Omeprazole enteric coated (OEC) pellets were coated first with a buffering and separating layer, and then with two additional layers, i.e. the floating generating system, described in Example 1. These omeprazole floating enteric coated (OFEC) pellets were then compressed with an effervescent excipient granulate into a tablet. When the tablet was dissolved in a glass of water the resulting effervescent solution had a pH value around 5.

Manufacture of OEC pellets were done according to principles described in WO96/01623.

Omeprazole enteric coated (OEC) pellets.

Preparation of cores:

| | |
|---|---|
| Magnesium omeprazole | 10.3 kg |
| Sugar sphere seeds | 10.3 kg |
| Hydroxypropyl methylcellulose | 1.5 kg |
| Purified water | 31 kg |

Separating layer:

| | |
|---|---|
| Cores from above | 12.0 kg |
| Hydroxypropyl cellulose | 1.2 kg |
| Talc | 2.1 kg |
| Magnesium stearate | 0.17 kg |
| Purified water | 24 kg |

Enteric coating layer:

| | |
|---|---|
| Pellets covered with separating layer | 12.0 kg |
| Methacrylic acid copolymer* | 5.3 kg |
| Triethyl citrate | 1.6 kg |
| Mono- and diglycerides | 0.3 kg |
| Polysorbate 80 | 0.03 kg |
| Purified water | 17.5 kg |

*Charged as a 30% dispersion (17.6 kg) containing this amount of polymer.

Over-coating layer:
(applied directly after enteric coating layer without discharge of material)

| | |
|---|---|
| Hydroxypropyl methylcellulose | 0.24 kg |
| Magnesium stearate | 0.007 kg |
| Purified water | 4.8 kg |

Omeprazole floating enteric coated (OFEC) pellets

Buffering and separating layer:

| | |
|---|---|
| OEC pellets according to above | 100 g |
| Hydroxypropyl methylcellulose | 4.5 g |
| Citric acid | 4.2 g |
| Purified water | 94 g |
| Ethanol 95% (w/v) | 94 g |

Gas generating layer:

| | |
|---|---|
| OEC-pellets with buffering separating layer | 100 g |
| Hydroxypropyl methylcellulose | 2.5 g |
| Sodium bicarbonate | 10 g |
| Purified water | 125 g |

Gas-barrier layer:

| | |
|---|---|
| Pellets with gas generating layer | 100 g |
| Hydroxypropyl methylcellulose acetate succinate LF | 10 g |
| Polyethylene glycol 400 | 2 g |
| Methanol anhydrous | 210 g |

The content of omeprazole in the obtained OFEC pellets was 158 mg/g pellets. Test of acid resistance as described in WO 96/01623 showed that 95% of the omeprazole content was intact after 2 hours exposure to 0.1 M HCl.

Omeprazole effervescent tablets 20 mg containing effervescent EC pellets
For 500 tablets the following ingredients were used;

| | grams |
|---|---|
| OFEC pellets | 63.5 |
| Citric acid anhydrous | 302.5 |
| Mannitol pwd | 150 |
| Aspartam | 15.0 |
| Polyvinylpyrrolidone (= PVP) | 3.5 |

Omeprazole effervescent tablets 20 mg containing effervescent EC pellets
For 500 tablets the following ingredients were used;

| | grams |
|---|---|
| Riboflavine | 0.15 |
| Ethanol 99.5% | 40 |
| Sodium laurylsulphate | 0.4 |
| Sodium stearylfumarate | 5 |
| Sodium bicarbonate | 244.5 |
| Essence orange pwd | 1.5 |

The mannitol, citric acid and aspartam were granulated with a solution of the PVP in the ethanol in which the colorant riboflavin had been added.

The wet mass was dried in a fluid bed drier. The granules obtained were milled to pass a 1.0 mm sieve.

A premix consisting of the sodium laurylsulphate, sodium stearylfumarate, essence orange and the OFEC pellets was mixed in a turbula mixer.

Final mixing was performed in a Kenwood mixer where the premix, the citric acid containing granules and the sodium bicarbonate were mixed to homogeneity. The final mixing time was 3 minutes.

Compression to tablets was done on a tableting machine equipped with punches giving 20 mm diameter flat tablets with bevelled edges. Tablet weight was 1572 mg.

Test of Tablets.

One effervescent tablet dissolved in 100 ml of purified water was observed. The result shows that after the effervescence was completed the OFEC pellets are floating for a couple of minutes.

Floating Behaviour

Comparison of pellets with and without floating generating system.

| | OEC (from Ex. 2.) | OFEC (with) (from Ex. 2.) |
|---|---|---|
| Density | g/ml | g/ml |
| | 1.25* | 1.29* |
| Test in solution obtained by dissolving the ingredients of one tablet excluding the pellets in 100 ml aq. Purif. (Density = 1.00 g/ml) | all are sinking | after 15–29 sec. all are floating |

*Micromeritics multivolume pycnometer 1305 operated with helium.

(Gasadsorption according to B.E.T.)

It is obvious that the floating not is achieved as an effect of that the density of the liquid is higher than the density of the OFEC pellet (before exposure to the liquid).

EXAMPLE 3

Effervescent tablets comprising enteric coated units of the (−)-enantiomer of omeprazole.

The tablets were manufactured as described in Example 2. Magnesium salt of the (−)-enantiomer of omeprazole was used instead of magnesium omeprazole in tablets prepared according to example 2.

EXAMPLE 4

Sachet containing omeprazole 20 mg as floating enteric coated pellets in an effervescent mixture.

Principle.

The omeprazole floating enteric coated (OFEC) pellets prepared as described in example 2 were filled together with effervescent excipients in a sachet.

| One sachet contained | |
|---|---|
| | mg |
| OFEC pellets | 127 |
| Citric acid anhydrous | 605 |
| Mannitol pwd | 300 |
| Aspartam | 30 |
| Polyvinylpyrrolidone (= PVP) | 7 |
| Riboflavine | 0.3 |
| Sodium laurylsulphate | 0.8 |
| Sodium stearylfumarate | 10 |
| Sodium bicarbonate | 489 |
| Essence orange pwd | 3 |

The mannitol, citric acid and aspartam were granulated in the same way and amounts as described in example 2 giving milled citric acid containing granules.

A premix consisting of the sodium laurylsulphate, sodium stearylfumarate, essence orange and the sodium bicarbonate was mixed in a turbula mixer.

Final mixing was performed in a Kenwood mixer, where the premix and the citric acid containing granules were mixed to homogeneity. The final mixing time was 3 minutes.

The sachets were first filled with the OFEC pellets, 127 mg, and then with the mixture of the effervescent components, 1445 mg.

Floating Behaviour

The content of one sachet dispersed into 100 ml of purified water was observed. The result showed that after the effervescence was completed (approx. 20 seconds) the OFEC pellets were floating and after another couple of minutes they are still floating.

EXAMPLE 5

Lansoprazole floating enteric coated pellets.

Principle.

Lansoprazole enteric coated (LEC) pellets were coated first with a buffering separating layer and then with two additional layers, i.e. the floating generating system, described in earlier examples (for instance Example 1), thus giving lansoprazole floating enteric coated (LFEC) pellets.

| Lansoprazole enteric coated (LEC) pellets | |
|---|---|
| Preparation of cores: | |
| Lansoprazole | 400 g |
| Non-pareil cores | 400 g |
| Hydroxypropyl methylcellulose | 80 g |
| Sodium laurylsulphate | 3 g |
| Water purified | 1360 g |
| Separating layer: | |
| Core material (acc. to above) | 100 g |
| Hydroxypropyl methylcellulose | 9 g |
| Polyethyleneglycol 6000 | 1 g |
| Talc | 18 g |
| Ethanol 95% | 250 g |
| Water purified | 250 g |

| -continued | |
|---|---|
| Lansoprazole enteric coated (LEC) pellets | |
| Enteric coating layer: | |
| Coated pellets (acc. to above) | 100 g |
| Hydroxypropyl methylcellulose phtalate | 39.9 g |
| Acetyltributyl citrate | 8 g |
| Cetanol | 2.1 g |
| Ethanol 95% | 162 g |
| Acetone | 378 g |

Suspension layering was performed in a fluid bed apparatus. Lansoprazole was sprayed onto inert non-pareil cores from a water suspension containing the dissolved binder.

The prepared core material was coated with a separating layer in a Wurster equipped fluid bed apparatus with the talc suspended in a HPMC solution.

Enteric coating was performed in the same equipment with a solution in organic solvents of the materials forming the enteric layer.

The enteric coated pellets were coated with a buffering and separating layer and the two layers forming the floating generating system, as described in example 2. The prepared floating enteric coated pellets were mixed with an effervescent granulate and filled into a sachet, as described in example 4.

EXAMPLE 6

Effervescent tablets comprising furosemid floating extended release pellets. Tablet strength 60 mg furosemid.

Principle.

Furosemid extended release (FER) pellets were coated with two additional layers, i.e. the floating generating system, together achieving a floating effect on the pellets when exposed for an acidic solution. The first layer comprises sodium bicarbonate as a gas source and the second layer is functioning as a gas barrier. The furosemid floating ER (FFER) pellets were then directly compressed with excipient into an effervescent tablet. When the tablet is dissolved in a glass of water, the effervescence results in a solution with a pH value around 4.

| Furosemid extended release (FER) pellets Furosemid cores were prepared by spray coating 3.0 kg of silicon dioxide particles with a suspension of 3.0 kg furosemid in a PVP/water solution (1.5 kg PVP + 5.6 kg water) in a fluidized bed coater. | |
|---|---|
| Extended release layer: | |
| Cores prepared as described above | 700 g |
| Hydroxypropyl cellulose | 105 g |
| Ethylcellulose | 245 g |
| Ethanol 95% | 3048 g |

The extended release layer was applied in a Wurster equipped fluidized bed. Particle size of the pellets obtained varied between 0.25 mm to 0.71 mm. A more detailed description is given in WO 96/01621.

| Furosemid floating extended release (FFER) pellets | |
| --- | --- |
| Gas generating layer: | |
| FER pellets according to above | 200 g |
| Hydroxypropyl methylcellulose | 20 g |
| Sodium bicarbonate | 80 g |
| Purified water | 1000 g |
| Gas-barrier layer: | |
| FER Pellets with gas-source layer | 100 g |
| Hydroxypropyl methylcellulose acetate succinate LF | 10 g |
| Polyethylene glycol 400 | 2 g |
| Methanol anhydrous | 210 g |

The FER pellets were coated with the bicarbonate solution in a Wurster equipped fluidized bed. The obtained product was then further coated with a second layer, i.e. the gas-barrier layer, in the same equipment. The FFER pellets were obtained.

| Preparation of furosemid effervescent extended release tablet. | |
| --- | --- |
| | mg/tabl. |
| FFER pellets prepared acc. to above | 373 |
| KHCO3 | 490 |
| Tartaric acid | 650 |
| Sorbitol | 400 |
| Sodium stearylfumarate | 0.5 |
| Sodium laurylsulphate | 1.0 |

First all excipients were thoroughly mixed. Thereafter the FFER pellets were added and mixing completed.

Flat tablets, 20 mm in diameter having bevelled edge, were compressed on a tableting machine. Tablet weight was 1914 mg.

Test of Tablet.

Dissolution rate of furosemid from the tablet was measured in 1000 ml phosphate buffer pH 6.8, 37 C, using USP dissolution apparatus 2 (paddle), operating at 100 r.p.m.

Figure 4:
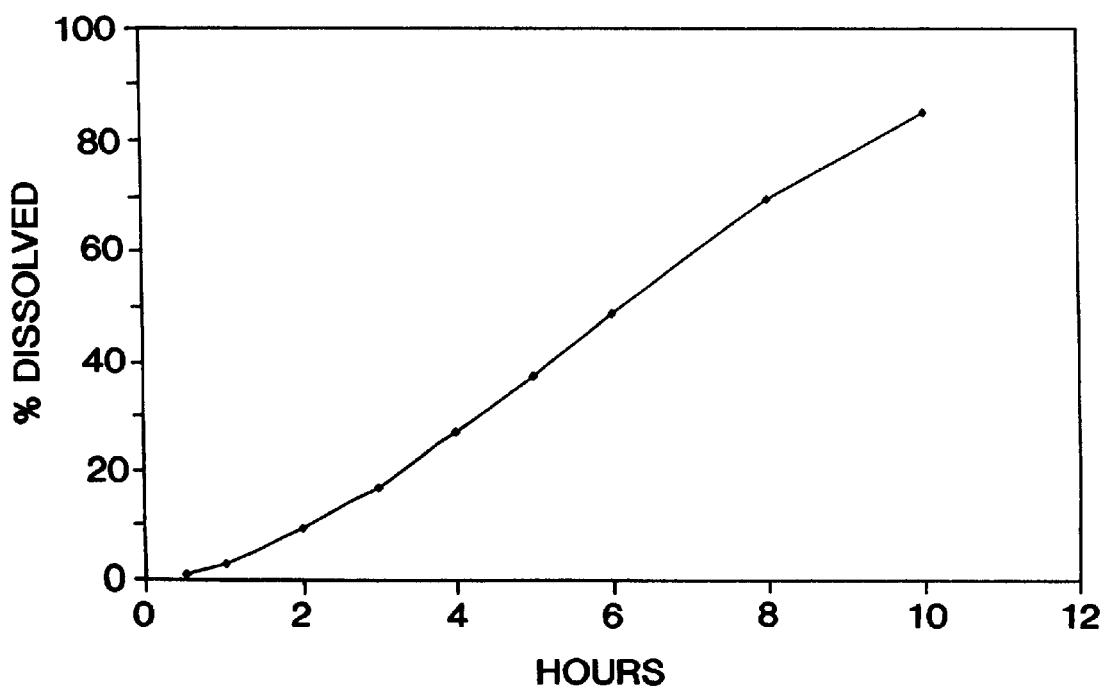
FIG. 4 shows the dissolution of furosemid from a tableted effervescent dosage for according to the present invention, as described in example 6 below.

The dissolution of furosemid from the effervescent tablet, average 3, is shown in FIG. 4.

Floating Behaviour

Comparison of pellets with and without a floating generating layer.

| | FER (from Ex. 6.) | FFER (with) (from Ex. 6.) |
| --- | --- | --- |
| Density * | 1.44 g/ml | 1.52 g/ml |
| Test in buffer pH 5 | all are sinking | after 15–20 sec. all are floating |

*Micromeritics multivolume pycnometer 1305 operated with helium.
(Gasadsorption according to B.E.T.)

What is claimed is:

1. An effervescent dosage form comprising, as a first component, effervescent excipients and as a separate second component, a plurality of individual units comprising a pharmaceutically active compound selected from the group consisting of a proton pump inhibitor and a beta blocking agent and optionally pharmaceutically acceptable excipients wherein each unit is provided with a floating generating system comprising at least two coating layers, one of which is a gas generating layer and the other layer is a barrier layer enclosing the generated gas, and wherein the first component is separated from the second component by the layers of the floating generating system.

2. The effervescent dosage form according to claim 1, wherein the gas generating layer is applied under the barrier layer.

3. The effervescent dosage form according to claim 1, wherein the gas generating layer comprises a water soluble binding agent and a carbon dioxide generating compound.

4. The effervescent dosage form according to claim 3, wherein the carbon dioxide generating compound is a carbonate or a bicarbonate.

5. The effervescent dosage form according to claim 1, wherein the gas generating layer comprises a water soluble binding agent and an oxygen generating compound.

6. The effervescent dosage form according to claim 1, wherein the barrier layer comprises a non-water soluble polymer and optionally a water soluble pore forming substance.

7. The effervescent dosage form according to claim 1, wherein the individual units comprises a separating layer applied under the gas generating layer separating the unit from the floating generating system.

8. The effervescent dosage form according to claim 1, wherein the proton pump inhibitor is selected from the group consisting of omeprazole, a pharmaceutically acceptable salt of omeprazole, the single enantiomers of omeprazole, and an alkaline salt of the single enantiomers of omeprazole.

9. The effervescent dosage form according to claim 1, wherein the beta blocking agent is metoprolol or a pharmaceutically acceptable salt thereof.

10. The effervescent dosage form according to claim 1, wherein the dosage form is an effervescent tablet comprising a plurality of individual coated units.

* * * * *